United States Patent [19]

Haberman et al.

[11] Patent Number: 5,251,488
[45] Date of Patent: Oct. 12, 1993

[54] MULTIPHASE VOLUME AND FLOW TEST INSTRUMENT

[75] Inventors: John P. Haberman; Gregory J. Hatton, both of Houston, Tex.

[73] Assignee: Texaco Inc., White Plains, N.Y.

[21] Appl. No.: 655,476

[22] Filed: Feb. 14, 1991

[51] Int. Cl.$^5$ .............................................. G01F 15/08
[52] U.S. Cl. ................................ 73/861.04; 73/61.44
[58] Field of Search ............... 23/61.43, 61.44, 861.04, 23/200, 311

[56] References Cited

U.S. PATENT DOCUMENTS

| | | | |
|---|---|---|---|
| 2,451,882 | 10/1948 | Smith | 73/61.43 |
| 3,220,930 | 11/1965 | Thompson | 73/61.44 |
| 3,344,659 | 10/1967 | Chambers | 73/61.44 |
| 3,464,258 | 9/1969 | Lerner | 73/61.44 |
| 3,721,121 | 3/1973 | Fierfort | 73/61.44 |
| 3,911,256 | 10/1975 | Jones . | |
| 3,935,741 | 2/1976 | Zinsmeyer | 73/311 |
| 4,672,840 | 6/1987 | Cullick . | |
| 4,760,742 | 8/1988 | Hatton | 73/861.04 |

Primary Examiner—Herbert Goldstein
Attorney, Agent, or Firm—Kenneth R. Priem; Ronald G. Gillespie

[57] ABSTRACT

An apparatus and a method for ascertaining the relative amount of two or more phases present in a multiphase flow, such as produced petroleum, through a pipe. Multiphase flow is temporarily diverted into a test section. Normal flow is then restored with fluids trapped in the test pipe. One or more floats of proper densities inside the test pipe are allowed to float to and stabilize at positions representative of the phase interfaces. An electromagnetic, radioactive, acoustic, or other sensor is used from outside the test pipe to locate the interfaces as indicated by the position of the floats. The relative amount of the various phases is then calculated. In an alternative embodiment, the velocity of a piston located inside the test section is also measured to give the total flow rate of the multiphase flow. The total volumetric flow rate, along with the relative phase amounts gives the absolute volumetric phase flow rates.

10 Claims, 2 Drawing Sheets

MULTIPHASE VOLUME AND FLOW TEST INSTRUMENT

BACKGROUND OF THE INVENTION

1. Field of the Invention

This invention relates to an apparatus and method for measuring the relative volumes of the various phases present in a multiphase stream, and, more particularly, to an improved apparatus and method capable of quickly and reliably determining the relative amounts of the various phases found in a multiphase stream, such as a stream of petroleum produced from an oil and gas well.

2. Description of the Related Art

It is often important to have a quick and reliable quantitative indication of the relative amounts of the various phases present in a stream containing multiple phases. Such streams are often encountered in a refinery or chemical plant. Without in any way limiting the application of the present invention, it is suggested that application of the present invention is of special benefit in the context of the production of petroleum from oil and gas wells.

Produced petroleum streams typically contain multiple phases. Prior to its production to the surface, petroleum in the reservoir contains varying amounts of dissolved gas. This gas separates from the liquid when the petroleum is brought to the surface and the pressure is released. A significant fraction of production wells, in addition, produce varying amounts of water at certain stages during their production lives. Thus, the typical oil well produces a stream which is made up of two or even three phases.

Without unduly elaborating on well known reservoir engineering principles, it is generally accepted that knowledge of the relative amounts of the various fluid phases, often expressed as the gas-oil-ratio (GOR) or water-oil-ratio (WOR), is often crucial to understanding a well. This knowledge is also one of the keys to decisions intended to optimize the commercial value of the well and reservoir from which the well is producing.

Knowledge of the relative amounts of the various phases can be obtained by observing the amount of water, oil and gas phases in a holding tank into which the production of the well is routed for storage. However, in typical operations, a number of nearby wells may be routed to the same tank, making it unfeasible to determine the relative amounts of the phases of the individual wells. Often also, well production from surrounding wells is piped directly into a field plant which again makes it unfeasible to gauge the performance of an individual well.

There has long been a need for an instrument or apparatus which could be installed in the field on or near the site of an operating well which would be able to periodically measure the relative amounts of the various fluid phases present.

SUMMARY OF THE INVENTION

Briefly, the present invention provides a new and improved apparatus or instrument for measuring the relative amounts of the various phases present in a petroleum well production stream. An apparatus according to the present invention is rugged so as to withstand the harsh environment often encountered in an oil field with little or no maintenance, and which can be operated remotely and/or automatically without the need for on-site field crew intervention.

In an alternative embodiment of the present invention, a new and improved apparatus is provided which can also measure the flow rate in addition to determining the relative amounts of the various phases present in the fluid.

In a preferred embodiment of the present invention, a test section of pipe of a desired length is provided, oriented substantially vertically, and connected at opposite ends to spaced positions of pipe carrying the well fluid production. A plurality of valves, one at each connection, are provided to quickly switch the flow path from the main pipe to the test section. Once the flow path fluid has filled the test section, the valves can again be actuated to restore flow through the main pipe, while retaining a sample of the multiphase fluid in the test section.

The fluids in the test section are allowed to settle or stand for a period of time sufficient to allow the fluid phases present to disengage and form distinct interfaces. In some situations, it may not be necessary to form a distinct interface, as is discussed below. It may also in some cases be necessary to aid the separation process by introducing chemical agents which tend to break up any emulsions present and lead to the rapid formation of distinct phases.

A plurality or suitable number of buoyant bodies, or floats, are present in the test section. The floats are each of a density intermediate between the densities of the various fluid phases expected. The floats tend to float to, and stabilize at, the interfaces between the various phases. Thus, for example, a float having a density intermediate between that of oil and that of gas will stabilize at the oil-gas interface. Similarly, a float having a density intermediate between that of oil and that of water will stabilize at the oil-water interface.

In some situations, if the floats are of the proper shape, size, density and the like, they can find an equilibrium position that is the same as the position they would find at an actual interface. This may be a mean density, or it may be empirically determined for any particular pair of places.

Once the floats have stabilized at or near the interfaces, the position of the various floats in the test section can be ascertained. The position of the floats in the test section is an indication of the interfaces. The interface position, taken with known geometry of the test section readily yields an indication of the relative amounts of the various phases. The position of the floats can be determined in a number of ways. One such method involves the inclusion of magnetic materials in the float. Passing a pick up coil along the outside of a preferably non-magnetic test section yields an indication of the position of the floats, particularly if the test pipe is made of a non-magnetic material.

In another embodiment of the present invention, a piston is also provided to measure the flow rate of the multiphase fluid in addition to determining the relative amounts of the various phases using the floats. The flow of fluid into the test pipe causes the piston to move through the test pipe. The time from the start of motion by the piston until arrival at a predetermined spaced point in the test section is measured, yielding for a known geometry of test pipe the total flow rate. The relative amounts of the phases are determined as in the previously summarized embodiment, giving, in addition to the total flow rate, the absolute flow rates of the various phases.

It may not always be necessary to allow the fluids to settle or stand for a period of time sufficient to allow the fluid phases present to disengage and form distinct interfaces. It bears pointing out that under some circumstances, floats of the proper size, shape, and density would locate themselves in their final equilibrium position even prior to, or even in the absence of, the formation of distinct interfaces. The optimal float density may be the mean density of the two fluid constituents or it may be determined empirically for various fluid pairs of interest.

One advantage of the present invention is that, unlike previously known methods, the measurement of the relative amounts of the phases (or the absolute flows of the phases in the case of the alternative embodiment) can be separately determined for each well of interest.

Another advantage of the present invention is that the determination can be conducted remotely and automatically, without the need for on-site field crew intervention.

DESCRIPTION OF THE PREFERRED EMBODIMENTS

Figure 1:
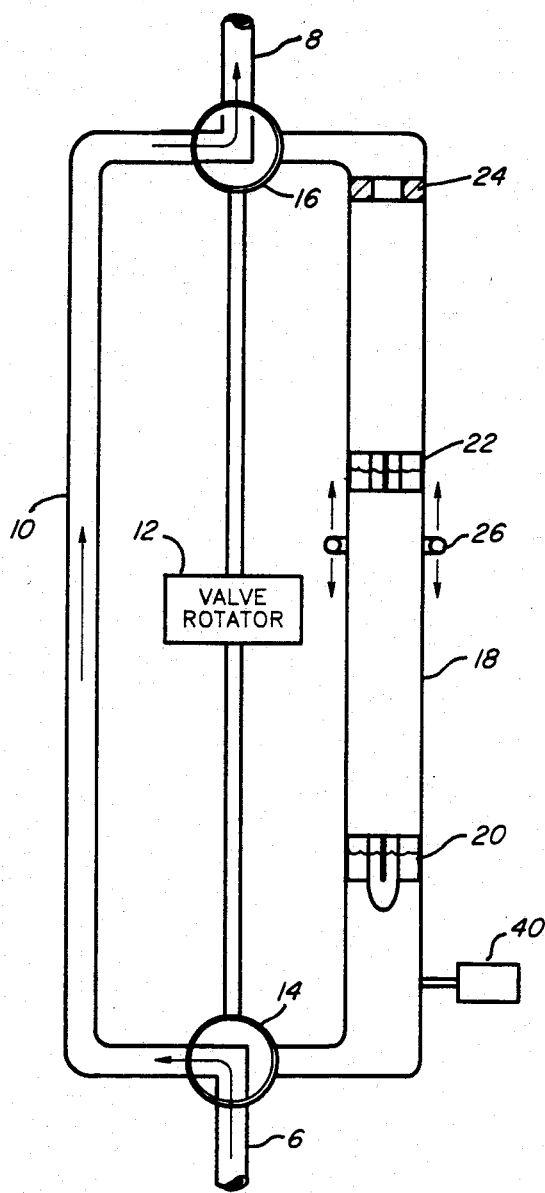
FIG. 1 is a schematic diagram, partly in cross-section, of a first embodiment of the present invention.

In the drawings, an apparatus A according to the present invention is shown in FIG. 1. Flow of a stream, usually containing petroleum (oil and/or gas) occurs normally vertically through a main pipe 10 between an inlet pipe 6 and an outlet pipe 8. At certain intervals, automatically set and/or upon remote activation, a valve actuator 12 is activated so as to simultaneously rotate both an inlet valve 14 between inlet pipe 6 and main pipe 10 and an outlet valve 16 connected to main pipe 10. Rotation of the valves 14 and 16 diverts flow from the main pipe 10 into a test section 18 which is substantially vertically oriented and which can be of any desired or optimal geometry.

Flow of the stream is allowed to proceed through the test section 18 for a period of time at least sufficient to completely displace the test section 18. Subsequently, the valve actuator 12 is again activated. The valves 14 and 16 are then reversed in position, stream flow to revert to its usual route through the main pipe 10. This actuation of the valves 14 and 16 traps an amount of fluids in the test section 18. These trapped fluids are then used to determine the relative amount of the various fluid phases present in the main pipe 10.

Figure 3:
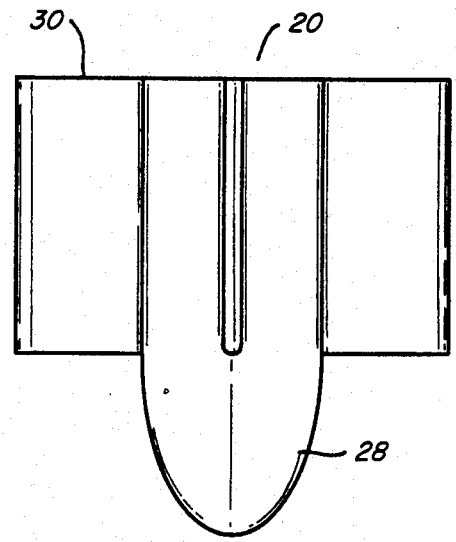
FIG. 3 is an elevation view of a float usable in the apparatus of FIGS. 1, 2A and 2B.

Permanently present in the test section 18 are one or more floats (FIG. 3). The number of floats used should equal the number of phases expected less one, i.e. should equal the number of interfaces to be expected in the stream being measured. For example, if a well is producing oil, gas and water, two floats should be used. If only oil and gas are expected, a single float will suffice. In the description which follows it is assumed that three phases are present. It is clear that the present invention can just as readily be applied when fewer or more than three phases are present.

A lower float 20 is designed to locate itself at a position representing the oil-water interface between these fluids in test section 18. To this end, the lower float 20 has an overall density intermediate between the densities of water and oil. Similarly, an upper float 22 is designed to locate itself at the oil-gas interface between these fluids in test section 18. To this end, the upper float 22 has an overall density intermediate between the densities of oil and gas.

The floats can be made of any convenient material and can assume any convenient shape. One of many possible shapes for the lower float 20 and upper float 22 is shown in FIG. 3 wherein most of the volume is located in the float body 28 toward the central portion of the float. Vanes 30 are used to centralize and stabilize the float during movement inside the test section 18. Another possible arrangement for the float (not shown) would place most of the volume on the outside, leaving a hole in the center, through which flow could pass.

One advantage of the float configuration shown in FIG. 3 is a lowered tendency of the float to become stuck to the side of the test section 18 as a result of the trapping of solids between the periphery of the float 20 and the internal walls of the test section 18.

Also shown in FIG. 1 is a float retainer or screen 24 near the top of the test section 18. The float retainer 24 is designed to retain the floats while the test section 18 is in full flow mode prior to the actuation of the valves 14 and 16 to trap fluids in the test section 18. During the full flow mode the floats 20 and 22 are forced by flow stream pressure against the float retainer 24. The shape of the floats 20 and 22 facilitates the flow of fluids in the test section 18. The fluids pass between the centralizing vanes 30 and past the test section float retainer or screen 24 leaving the system through the outlet valve 16. The float retainer or screen 24 is preferably constructed so that a central solid portion is attached to the inside walls with the aid of a number of vanes. While the solid central portion of the retainer or screen 24 serves to block the passage of the float, the fluids are able to flow through the spaces between the vanes near the periphery of the test section 18.

It may occur that the fluids to be measured form emulsions. This can occur either naturally or can be induced by the turbulent flow conditions encountered in the pipe. These emulsions may exhibit high stability and thus resist rapid separation into distinct phases. Such behavior may reduce the reliability of the measurement of the relative amounts of the various phases. It may be desirable in using the apparatus of the present invention on certain petroleum fluids, to use a chemical additive, such as a de-emulsifier, to break up the emulsion and bring about the rapid formation of distinct phases with clear interfaces. The additive may be added from a de-emulsifier vessel 40 connected to the test section 18. The mixing produced by the turbulence inside the test pipe 18 should be sufficient to assure rapid and thorough mixing of the de-emulsifier in the fluids. Alternative mixers (not shown) may be used to augment the mixing.

Other means may be used to break up any emulsions which may be present. For example, acoustic or electrical means, as is known, may effectively break up emulsions.

Once the test section 18 is sealed by valve rotator 12 changing the position of the valves 14 and 16 and fluid flow is resumed through the main pipe 10, sufficient time is allowed to elapse so as to assure that the phases present will separate sufficiently that the positions of the floats accurately represent the volumes of the phases. As described, the test pipe section 18 is oriented substantially vertically so as to take advantage of gravitational forces in separating the phases. As will be apparent to those skilled in the art, other equivalent techniques may be used. For example, the test section 18 could be located in a centrifuge which will bring about phase separation without relying on gravitational forces.

The position of the interfaces as indicated by the position of the floats can now be detected. A number of ways of detecting the position of the floats will readily occur to those skilled in the art. Without in any way limiting the scope of the present invention, several methods will be briefly discussed by way of example only.

In one example, the centralizing vanes 30 of the float would be made of material which either is, or which contains, magnetic material having sufficiently strong magnetic fields so as to penetrate the nonmagnetic casing of the test section 18. After float stability has been achieved, a sensor or detector 26, such as a toroidal inductive coil is passed along the outside of the test section 18. The coil or coils of detector 26 are moved along the outside of the test section 18 with the aid of a suitable transport mechanism with position indicator (not shown). As the moving detector 26 passes the magnetic material of the floats 20 and 22, perceptible magnetic signatures are sensed. The position indicator is then capable of recording the location of the sensor 26 when the signatures occur. The location readings can then be connected to a signal processor or computer. With such a computer, one can determine, based on the known geometry of test pipe 18 and the readings of sensor 26, the location of the interface to a volume or volume fraction of the various phases. The results of the determination are thereafter available to remote monitoring facilities for recording and/or to processing engineers on demand.

Another means for detecting the location of the interfaces would include using radiation sources on the floats and radiation detectors on the outside of the test pipe. Yet another means involves using sonic devices to detect the location of the floats. Many additional techniques for accomplishing the same ends will also be apparent to those skilled in the art. For example, the location of the separated phases may be determined by methods not employing floats. Examples may include ultrasonic techniques or techniques employing density measurements via nuclear instrumentation or differential pressure transducers.

Another apparatus A-1 of the present invention (FIG. 2A & 2B) is able to measure the total flow rate of the stream in addition to the relative amounts of the various phases. Knowing the total stream flow rate as well as the relative amounts of the various phases makes it possible to determine the absolute flow rates of each of the phases.

Figure 2A:
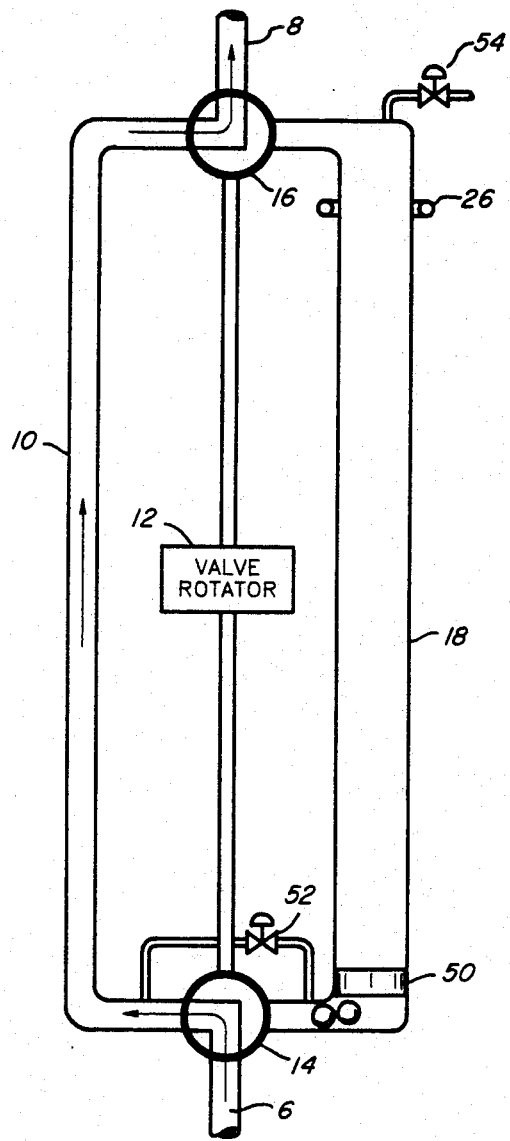
FIG. 2A is a schematic diagram, partly in cross-section of an alternative embodiment of the present invention at the start of an operating cycle.
Figure 2B:
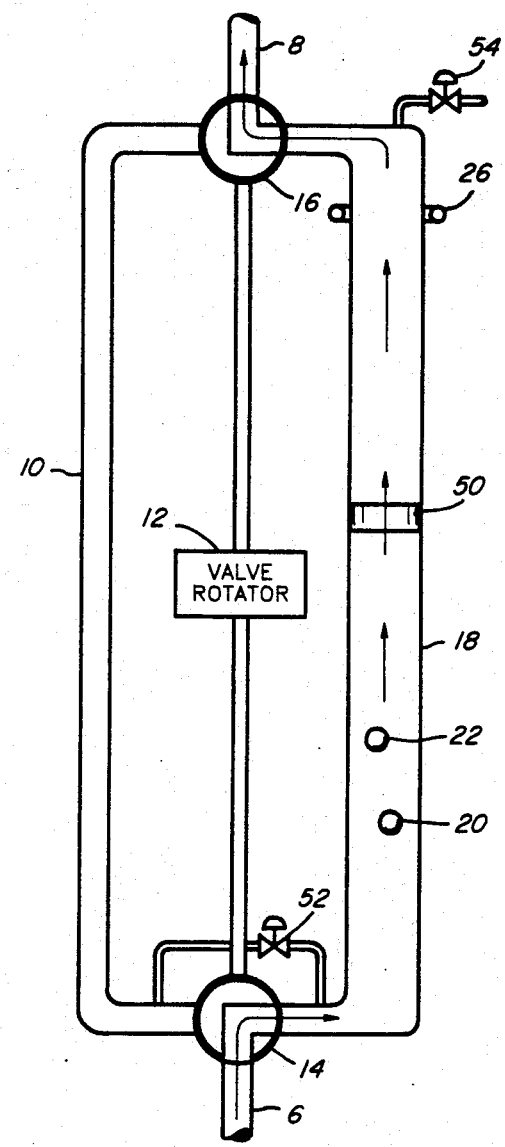
FIG. 2B is a schematic diagram, partly in cross-section, of the embodiment of FIG. 2A at the conclusion of a flow measuring cycle.

In the embodiment of FIGS. 2A and 2B, measurement of the relative amount of phases present occurs in a like manner to the embodiment of FIG. 1. Accordingly, like structure performing like functions bears like reference numerals. In addition, the embodiment of FIGS. 2A and 2B is able to measure the overall flow rate in main pipe 10. A movable, at least partially magnetic, piston 50 is provided in test section above the floats 22. At rest, piston 50 is located at a starting position near the bottom of the test section 18. The testing sequence is started by switching the production flow valves 14 and 16 so that the full flow is passed through the test section 18. This flow causes the piston 50 to rise in the test section 18. The piston 50 subsequently reaches an arrival location in an upper point of test section 18 at which the sensor 26 is initially located.

The arrival of the magnetic piston 50 at the sensor 26 causes an electric current to be induced in the sensor 26. At this time, valves 14 and 16 are activated to rapidly resume flow through the main pipe 10. Simultaneously, the time at which the piston 50 reaches the sensor 26 is recorded and subtracted from the time the sequence was started. This time difference gives the amount of time it took the piston 50 to rise from its rest position to the location of the sensor 26 near the top of the test section 18. The measured time of travel, together with the known travel distance based on the geometry of test section 18, is then used to determine the overall flow rate.

Sufficient time is allowed to elapse so as to allow the floats 20 and 22 to stabilize at positions representative of the phase interfaces. The location of the phase interfaces is then determined in the same manner as the embodiment of FIG. 1. It should be noted that the floats of the embodiment in FIGS. 2A and 2B can be similar to those used in FIG. 1. Alternatively, the floats can be of a wide range of shapes and configurations. Because flow is redirected to the main pipe 10 as soon as the piston 50 arrives at the sensor 26, the float retainer 24 used in the basic embodiment can be eliminated, as it is unnecessary. The configuration of the floats of the alternative configuration thus can take on virtually any convenient configuration.

Once the position of the floats has been determined, the piston 50 is returned to its original position near the bottom of the test pipe 18 by opening a bottom auxiliary valve 52 and a top auxiliary valve 54 in test section 18. A suitable fluid, such as water can then be pumped through the top auxiliary valve 54 into the test section 18 at sufficiently high pressures, exiting at bottom valve 52, to cause the piston 50 to return to its original position near the bottom of the test section 18. The auxiliary valves 52 and 54 are then closed, returning the apparatus A-1 to its initial pretest condition, ready for the next test cycle to commence.

The ability to measure both the flow rate and the relative volumes of the various phases automatically compensates for the "slip" of the gas phase with respect to the liquid phase, i.e., the extent to which the gaseous phase outruns the liquid phase. This is because the measurement according to this embodiment of the present invention involves sampling the production stream using the same criteria as are used downstream, as at a storage or treatment vessel, when the phases are separated and the amount of each phase per unit time is measured for commercial and accounting purposes.

In summary, therefore, it can be seen that the present invention and the embodiments disclosed herein are well adapted to carry out the objectives set forth. Certain changes can be made in the method and apparatus without departing from the spirit and the scope of this invention. It is realized that changes are possible and it is further intended that each element recited in any of the following claims is to be understood as referring to all equivalent elements for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

Those skilled in the art may find many variations and adaptations thereof, and all such variations and adaptations, falling within the true scope and spirit of applicants' invention, are intended to be covered thereby.

What is claimed is:

1. An apparatus for determining volumetric flow rates of phases in multiphase fluid flow through a main pipe, comprising:
   (a) a test section connected at spaced points to the main pipe;
   (b) switching means at spaced points of said test section capable of directing fluid flow through said test section or through the main pipe;
   (c) a float inside said test section capable of locating at least one interface between the fluid phases, and whose position in said test section is capable of being determined;
   (d) a piston located at a starting position in said test section and movable from said starting position by the multiphase fluid flow in said test section;
   (e) sensing means for detecting arrival of said piston at an arrival location spaced from said starting position in said test section and for determining the location of said float in said test section.

2. The apparatus of claim 1, further comprising:
   auxiliary valves at spaced positions in said test section to permit movement of said piston to said starting position in said test section from said arrival location.

3. An apparatus as in claim 1, wherein said switching means comprises simultaneously actuated valves.

4. An apparatus as in claim 1, wherein said sensing means is a coil and said float contains magnetic material.

5. An apparatus as in claim 1, wherein said sensing means is a radiation detector and said float contains radioactive material.

6. An apparatus as in claim 1, wherein said float includes a sonic emitter or reflector and wherein said sensing means is a sonic detector.

7. An apparatus as in claim 1, further comprising:
   means for injecting a chemical additive into said test section.

8. An apparatus as in claim 1 further comprising:
   means for introducing acoustical energy into said test section.

9. An apparatus as in claim 1 further comprising:
   means for introducing electrical energy into said test section.

10. A process for determining absolute volumetric flow rate of phases in multiphase fluid flow through a main pipe, comprising:
    (a) diverting the multiphase fluid flow into a test section connected at spaced points to the main pipe;
    (b) allowing a piston located in said test section to move to an arrival location in said test section;
    (c) measuring time elapsed from said diversion of the multiphase fluid flow to said test section till the reaching of said arrival location by said piston;
    (d) determining the total flow rate using said measured elapsed time;
    (e) allowing a float inside said test section to stabilize at a position representative of an interface between the multiphase fluids;
    (f) detecting the location of said float;
    (g) determining the relative volumes of the fluid phases based on said determined float locations; and
    (h) determining the absolute phase flow rate of the phases based on said measured elapsed times.

* * * * *